United States Patent
Amiard et al.

[11] 4,224,371
[45] Sep. 23, 1980

[54] SODIUM 3-ACETOXYLMETHYL-7-[2-(2-AMINO-4-THIAZOLYL)-2-METHOXYIMINO-ACETAMIDO]-CEPH-3-EME-4-CARBOXYLATE

[75] Inventors: Gaston Amiard, Noisy-le-Sec, France; Dieter Bormann, Kelkheim; Walter Duerckheimer, Hattersheim, both of Fed. Rep. of Germany; Jean Jolly, Fontenay-sous-Bois, France

[73] Assignee: Roussel Uclaf, Paris, France

[21] Appl. No.: 932,437

[22] Filed: Aug. 10, 1978

[30] Foreign Application Priority Data

Aug. 17, 1977 [FR] France .................. 77 25142

[51] Int. Cl.³ .................. A61K 31/545; C07D 501/34
[52] U.S. Cl. .................. 424/246; 544/27; 544/20
[58] Field of Search .................. 544/28; 424/246

[56] References Cited

U.S. PATENT DOCUMENTS

| | | | |
|---|---|---|---|
| 3,970,651 | 7/1976 | Kaplan et al. | 424/246 |
| 3,985,747 | 10/1976 | Kaplan et al. | 424/246 |
| 4,006,138 | 2/1977 | Yang | 424/246 |
| 4,098,888 | 7/1978 | Ochiai et al. | 544/21 |
| 4,152,432 | 5/1979 | Heymes et al. | 424/246 |

*Primary Examiner*—Paul M. Coughlan, Jr.
*Attorney, Agent, or Firm*—Hammond & Littell, Weissenberger and Muserlian

[57] ABSTRACT

Novel stable crystalline hydrate of D form of the syn isomer of sodium 3-acetoxymethyl-7-[2-(2-amino-4-thiazolyl)-2-methoxyimino-acetamido]-ceph-3-eme-4-carboxylate having the formula

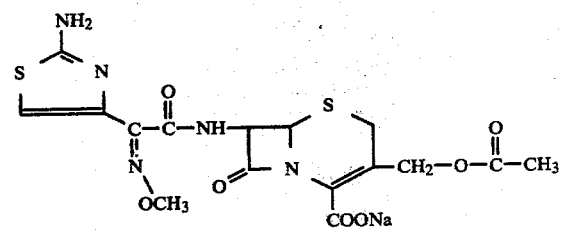

which has excellent antibiotic activity against both gram negative and gram positive bacteria and a process for its preparation.

4 Claims, 1 Drawing Figure

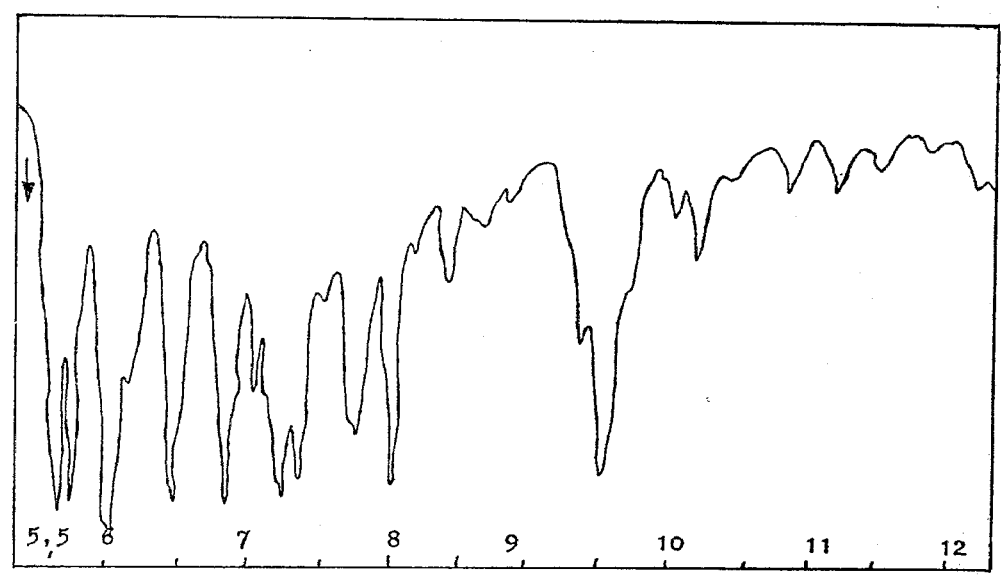

SODIUM 3-ACETOXYLMETHYL-7-[2-(2-AMINO-4-THIAZOLYL)-2-METHOXYIMINO-ACETAMIDO]-CEPH-3-EME-4-CARBOXYLATE

STATE OF THE ART

Copending, commonly assigned U.S. patent application Ser. No. 817,114 filed July 19, 1977, now U.S. Pat. No. 4,152,432 describes the syn isomer of 3-acetoxymethyl-7-[2-(2-amino-4-thiazolyl)-2-methoxyimino-acetamido]-ceph-3-eme-4-carboxylic acid and its sodium salt which have a remarkable antibiotic activity against gram negative and gram positive bacteria.

OBJECTS OF THE INVENTION

It is an object of the invention to provide a crystalline hydrated D form of the compound of formula I which is more stable and to a novel process for its preparation.

It is another object of the invention to provide novel antibiotic compositions and to a novel method of combatting bacterial infections in warm-blooded animals.

These and other objects and advantages of the invention will become obvious from the following detailed description.

THE INVENTION

The novel compound of the invention is the stable crystalline hydrate of D form of the syn isomer of sodium 3-acetoxymethyl-7-[2-(2-amino-4-thiazolyl)-2-methoxyimino-acetamido]-ceph-3-eme-4-carboxylate having the formula

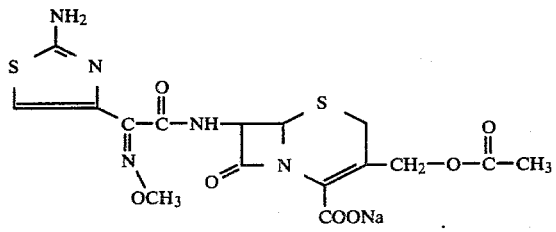

which has the infrared spectrum in nujol of FIG. 1 and has the following X-ray powder diffraction diagram obtained with the Kα copper radiation at a wave length of =1.54 A° wherein inter-reticular intervals are indicated as d and the relative intensities are indicated as $I/I_1$:

| d | $I/I_1$ |
|---|---|
| 9.3 | 0.95 |
| 8.8 | 0.09 |
| 6.5 | 0.07 |
| 6.46 | 0.06 |
| 6.10 | 0.13 |
| 5.30 | 0.25 |
| 5.12 | 0.05 |
| 5.03 | 0.04 |
| 4.57 | 0.04 |
| 4.40 | 0.17 |
| 4.20 | 0.29 |
| 3.96 | 0.70 |
| 3.88 | 0.18 |
| 3.76 | 0.34 |
| 3.6 | 1.00 |
| 3.41 | 0.15 |
| 3.27 | 0.09 |
| 3.19 | 0.11 |
| 3.13 | 0.13 |

| d | $I/I_1$ |
|---|---|
| 3.10 | 0.13 |
| 3.03 | 0.15 |
| 2.97 | 0.06 |
| 2.78 | 0.07 |
| 2.72 | 0.04 |
| 2.69 | 0.04 |
| 2.60 | 0.19 |
| 2.50 | 0.11 |
| 2.44 | 0.05 |
| 2.40 | 0.08 |
| 2.32 | 0.09 |
| 2.25 | 0.05 |

The crystalline sodium salt of the syn isomer of 3-acetoxymethyl-7-[2-(2-amino-4-thiazolyl)-2-methoxyimino-acetamido]-ceph-3-eme-4-carboxylic acid was previously obtained in other identifiable crystalline forms and the present crystalline D form is more stable than the previously obtained crystalline forms. The novel product of the invention occurs in the form of colorless solid which possesses a low affinity to atmospheric humidity and has a very remarkable stability.

The novel process of the invention to form the crystalline hydrated compound of the formula I comprises either (A) treating the syn isomer of 3-acetoxymethyl-7-[2-(2-amino-4-thiazolyl)-2-methoxyimino-acetamido]-ceph-3-eme-4-carboxylic acid or its hydrate, its ethanol solvate, its formic acid solvate or mixtures of hydrate and ethanol or formic acid solvate with a sodium salt of the formula $$NaX \qquad II$$

wherein X is anion of an acid with an acidity equal to or less than the treated ceph-3-eme-4-carboxylic acid and crystallizing the hydrated salt of formula I formed in situ in the presence, if necessary, of an excess of an organic solvent in which the said sodium salt is practically insoluble or (B) reacting the syn isomer of 3-acetoxymethyl-7-[2-(2-amino-4-thiazolyl)-2-methoxyimino-acetamido]-ceph-3-eme-4-carboxylic acid or in the form of its hydrate, its ethanol solvate or its formic acid solvate or mixtures of hydrate and solvate with a sodium salt of an organic carboxylic acid in methanol and crystallizing the sodium salt of formula I in the form of its methanol solvate which can be changed, if desired, into the said sodium salt without any methanol and then, hydrate the said sodium salt or its methanol solvate.

The preparation of the syn isomer of 3-acetoxymethyl-7-[2-(2-amino-4-thiazolyl)-2-methoxyimino-acetamido]-ceph-3-eme-4-carboxylic acid, of its formic acid solvate and of a mixture of this solvate with the hydrated form is described in Belgium Pat. No. 850,662. Its ethanol solvate may be obtained by treating the formate of the acid with ethanol and the hydrate of the said acid and a mixture of the said hydrate and the said ethanol solvate may be obtained, respectively, by permitting contact of the said acid and its ethanol solvate with humid air.

The salts of formula II may be the sodium salt of mineral acids or organic acids. Examples of suitable mineral acid salts are sodium bicarbonate, sodium carbonate and trisodium phosphate. Examples of suitable carboxylic acids for the sodium salts are straight or branched chain, saturated or unsaturated aliphatic carboxylic acids of 1 to 18 carbon atoms, preferably 2 to 10 carbon atoms, optionally interrupted in the aliphatic chain with one or more heteroatoms such as oxygen or sulfur and optionally substituted with an aryl such as phenyl, thienyl or furyl or with one or more members of the group consisting of hydroxyl, halogen such as fluorine, chlorine or bromine, especially chlorine, carboxyl groups, lower alkoxycarbonyl such as methoxycarbonyl, ethoxycarbonyl or propyloxycarbonyl or aryloxy such as phenoxy. Equally useful are sufficiently soluble aromatic carboxylic acids such as substituted benzoic acids, preferably lower alkyl substituted benzoic acids.

Examples of specific organic carboxylic acids are formic acid, acetic acid, acrylic acid, butyric acid, adipic acid, isobutyric acid, isocaproic acid, chloropropionic acid, crotonic acid, phenylacetic acid, 2-thienylacetic acid, 3-thienylacetic acid, 4-ethylphenylacetic acid, glutaric acid, monoethyl adipate, hexanoic acids, heptanoic acids, decanoic acids, oleic acid, stearic acid, palmitic acid, 3-hydroxypropionic acid, 3methoxypropionic acid, 3-methylthiobutyric acid, 4-chlorobutyric acid, 4-phenylbutyric acid, 3-phenoxybutyric acid, 4-ethyl-benzoic acid and 1-propyl-benzoic acid. The preferred sodium salts are sodium acetate, sodium 2-ethylhexanoate and sodium diethylacetate, most preferably sodium acetate. The sodium salts may be used as they are or may be prepared in situ depending on their solubility.

The sodium salts of formula I may be prepared in different ways. In variation A above, the ceph-3-eme-4-carboxylic acid is added to an aqueous solution of the sodium salt of formula II and the reaction product is crystallized in the presence of organic solvents in which the sodium salt of the ceph-3-eme-4-carboxylic acid is practically insoluble. When the formation of the salt is achieved, the precipitating solvent is added sufficiently slowly so that the sodium salt does not begin to precipitate in the amorphous form. Water miscible alcohols or ketones such as methanol, ethanol, n-propanol, isopropanol or acetone are suitable organic solvents to be used in the reaction.

In a preferred embodiment of modification A, the sodium salt of formula II is placed in a mixture of water and organic solvent and the acid ceph-3-eme-4-carboxylic acid is added thereto and after the said acid is dissolved therein, crystallization of the sodium salt is effected eventually by adding to the mixture an excess of the organic solvent in which the sodium salt is nearly insoluble, the said crystallization being sufficiently slow that the sodium salt does not precipitate in an amorphous form.

The ratio of water and organic solvent in the mixture may be varied to a certain degree with from 1 part of water to 5 parts of organic solvent to about 1 part of water to 9 parts of organic solvent being preferred to obtain a crystalline product with a high yield. For the same reason, the sodium salt of formula II is preferably used in stoichiometric amounts but in some cases, it is advantageous to use an excess of the sodium salt of formula II of about 10 to 200%, preferably about 20% excess.

The formation of the sodium salt may be formed at different temperatures. However, in order to have a manipulation which does not alter the desired product, for example, to avoid a rapid crystallization, it is recommended to effect the formation of the desired sodium salt at a temperature of 0° C. or less and effect the crystallization at a temperature greater than 0° C., preferably about 10° to 25° C. However, the sodium salt may equally be prepared in a comparable yield at room temperature.

The crystals of the desired sodium salt of the invention prepared by the process of the invention are in the stable D form.

In a preferred modification of process A, if aqueous methanol is used as solvent in the reaction of sodium salt formation, firstly the sodium salt, preferably sodium acetate, is dissolved in aqueous methanol at about 0° C., then the syn isomer of 3-acetoxymethyl-7-(2-(2-amino-4-thiazolyl)-2-methoxyimino-acetamido)-ceph-3-eme-4-carboxylic acid, or its hydrate, ethanol solvate, formic acid solvate or a mixture of hydrate and solvate is slowly introduced thereto and then the mixture is stirred at 0° C. If desired the resulting solution may also be passed through a sterilizing filter.

The crystallization phase of the D form is preferably effected by pouring the resulting solution into a solvent in which the desired sodium salt is practically insoluble. The solvent may be a water-miscible organic solvent containing 0.5 to 10% of water such as n-propanol, isopropanol, tert.-butanol, acetone or preferably ethanol.

In modification B of the process of the invention, the syn form of 3-acetoxymethyl-7-[2-(2-amino-4-thiazolyl)-2-methoxyimino-acetamido]-ceph-3-eme-4-carboxylic acid per se or its hydrated form or its ethanol solvate or its formic acid solvate or mixtures of its hydrate and its ethanol or formic acid solvate is reacted with a sodium salt of an organic aliphatic or aromatic carboxylic acid in methanol to form the said sodium salt in methanol. The preferred sodium salts used are sodium acetate, sodium 2-ethylhexanoate or sodium diethylacetate.

In this variation, the crystalline compound is obtained in the form of its methanol solvate which can be transformed into the sodium salt not containing methanol by intensive drying, for example at 30° to 50° C. under reduced pressure resulting in hygroscopic crystals of the sodium salt.

The methanol solvate as well as the non-solvated product not containing methanol may be hydrated to form the stable form D which is desired. The hydration may be effected in different ways such as by maintaining the product under very humid conditions in air or atmosphere such as nitrogen or suspending the product to be hydrated in a water-miscible organic solvent containing 1 to 10% of water. In the latter way, the organic solvent may be a ketone such as acetone or an alcohol such as ethanol, n-propanol, isopropanol or tert.-butanol.

In a preferred variant of the said process, the sodium salt is suspended in ethanol containing 1 to 10% of water and the suspension is stirred at room temperature for 10 to 30 hours. In this manner, the methanol solvate or the sodium salt not containing methanol is transformed in a manner suitable to form the stable crystalline phase, said "D form", of the sodium salt. The amount of water in the crystalline D form depends upon the humidity of the media and may be up to 15% without modifying the crystalline structure. By drying, particularly under reduced pressure at room temperature, the amount of water may be reduced to the preferred range of about 3 to about 6%.

The crystalline hydrate of the D form may also be prepared by treating the said syn isomer of the free acid in its non-solvated form, its hydrated form, its ethanol solvate form, its formic acid solvate form or mixtures of the hydrate and its ethanol solvate or formic acid solvate with a sodium salt of an organic acid in methanol, recovering the crystalline methanol solvate of the sodium salt, suspending the said methanol solvate in a water miscible organic solvent containing a small amount of water and letting the suspension remain to recover the hydrated crystalline D form of the syn isomer of the sodium salt. Preferably the sodium salt is sodium acetate, sodium ethylhexanoate or sodium diethylacetate. The water miscible solvent containing a small amount of water is preferably ethanol containing 1 to 10% of water. The conditions of the procedure permit one to use sterile conditions.

The novel antibiotic compositions of the invention are comprised of an antibiotically effective amount of the hydrated crystalline D form of the syn isomer of sodium 3-acetoxymethyl-7-[2-(2-amino-4-thiazolyl)-2-methoxyimino-acetamido]-ceph-3-eme-4-carboxylate with the above X-ray diffraction and infrared spectrum of FIG. 1 and a pharmaceutical carrier or excipient. The compositions may be in the form of tablets, dragees, gelules, granules, suppositories, injectable solutions or suspensions, pomades, cremes and gels prepared in the usual manner.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, diverse wetting agents, emulsifiers or dispersants and preservatives. The compositions of the invention possess very good antibiotic activity against gram positive bacteria such as staphylococcus, streptococcus, particularly penicillin resistant staphylococcus as well as against gram negative bacteria such as coliform bacteria, Klebsiella, Salmonella and Proteus.

The compositions are therefore useful in the treatment of germ sensitive infections and particularly those of staphylococcia such as staphylococcal septicemia, staphylococcia malignant on the face or skin, pyodermatitis, septic or suppurantes sores, anthrax, phlegmons, eresipels, acute primitive or post-grip staphylococcia, bronchopneumonia or pulmonary suppurations. They are equally useful for the treatment of collibacillosis and associated infections, infections of Proteus, Klebsiella and Salmonella and other infections caused by gram negative bacteria.

The novel method of the invention for combatting bacterial infections in warm-blooded animals, including humans, comprising administering to warm-blooded animals an antibacterially effective amount of the compound of formula I. The compound may be administered orally, rectally, parenterally or locally by topical application to the skin or mucous. The usual daily dose is 5 to 80 mg/kg depending on the method of administration.

In the following examples there are described several preferred embodiments to illustrate the invention. However, it is to be understood that the invention is not intended to be limited to the specific embodiments.

EXAMPLE 1

D form of syn isomer of crystalline sodium 3-acetoxymethyl-7-[2-(2-amino-4-thiazolyl)-2-methoxyimino-acetamido]-ceph-3-eme-4-carboxylate STEP A: crystalline methanol solvate of the syn isomer of sodium 3-acetoxymethyl-7-[2-(2-amino-4-thiazolyl)-2-methoxyimino-acetamido]-ceph-3-eme-4-carboxylate 3000 g of the syn isomer of 3-acetoxymethyl-7-[2-(2-amino-4-thiazolyl)-2-methoxyimino-acetamido]-ceph-3-eme-4-carboxylic acid [produced as in Belgium Pat. No. 850,662] containing 5% of ethanol and 0.9% of water were added all at once to a solution of 432 g of anhydrous sodium acetate in 12 liters of acetone and the mixture was stirred under nitrogen at 18°-20° C. for 5 minutes to obtain a practically total solution which was then placed in a reactor under a nitrogen pressure of 1.5 to 2.0 bars. A solution of 864 g of anhydrous sodium acetate in 4.5 l of methanol was added all at once at 18°-20° C. to the reactor with very effective agitation under a nitrogen atmosphere to obtain a limpid solution which was kept stirred under nitrogen at 18°-20° C.

A sample of 10 ml of the reactor solution was taken and crystallization was induced by scratching and the resulting suspension added back to the reaction mixture to induce crystallization after about 5 minutes. The mixture was rapidly stirred under nitrogen for 4 hours at 18°-20° C. and crystallization progressively increased. The suspension was then cooled to 0° to 2° C. and was then stirred for 2 hours and was vacuum filtered. The recovered product was empasted 3 times with one liter of anhydrous pure methanol at 0° to 2° C., then once with 1.5 liters of said methanol. The product was then dried at 20°-22° C. under reduced pressure for 48 hours to obtain 2,630 g of crystalline methanol solvate of the syn isomer of sodium 3-acetoxymethyl-7-[2-(2-amino-4-thiazolyl)-2-methoxyimino-acetamido]-ceph-3-eme-4-carboxylate containing 1% of water (by Fischer) and 8% of methanol (vapor phase chromatography). The product obtained was passed through a screen for homogenization.

STEP B: D form of syn isomer of crystalline sodium 3-acetoxymethyl-7-[2-(2-amino-4-thiazolyl)-2-methoxyimino-acetamido]-ceph-3-eme-4-carboxylate A mixture of 100 g of the screened product of Step A in 800 ml of ethanol containing 5% of water was stirred at 20°±2° C. for 15 to 20 hours and was then vacuum filtered. The recovered product was washed with 100 ml of 95% ethanol and was dried in an oven at 20°-25° C. under reduced pressure to obtain 99 g (uncorrected weight) of the D form of the syn isomer of crystalline sodium 3-acetoxymethyl-7-[2-(2-amino-4-thiazolyl)-2-methoxyimino-acetamido]-ceph-3-eme-4-carboxylate containing 5.3% water and less than 0.2% of methanol and less than 0.2% of ethanol. The product presented the above-indicated infrared spectrum and the above mentioned X-ray diffraction spectrum.

EXAMPLE 2

A solution of 6 g of sodium acetate in 20 ml of water was added with stirring at 20° C. to 50 ml of 98% ethanol and with continued stirring 25 g of an ethanol solvate of the syn isomer of 3-acetoxymethyl-7-[2-(2-amino-4-thiazolyl)-2-methoxyimino-acetamido]-ceph-3- eme-4-carboxylic acid were added thereto. After dissolution occured, the solution was cooled to 0° C. and 50 ml of 98% ethanol were added thereto dropwise with stirring. Activated carbon was added to the solution which was then filtered and the filtrate was heated to 20° C. Crystallization spontaneously occured shortly thereafter and filtration by aspiration was effected at room temperature 16 hours later. The recovered product was washed with a 1-7 water-ethanol mixture, with ethanol and then with ether to obtain colorless crystals of the D form of the syn isomer of sodium 3-acetoxymethyl-7-[2-(2-amino-4-thiazolyl)-2-methoxyimino-acetamido]-ceph-3-eme-4-carboxylate which after drying under reduced pressure contained 4.8% of water (by Fischer). The spectrum of X-ray diffraction and the infrared spectrum in nujol confirmed the D form.

EXAMPLE 3

The identical process of Example 2 was repeated except sodium 2-ethylhexanoate was used instead of sodium acetate to obtain crystals of the same product which were dried under reduced pressure. The infrared spectrum in nujol confirmed the stable D form.

EXAMPLE 4

5.01 g of the ethanol solvate of the syn isomer of 3-acetoxymethyl-7-[2-(2-amino-4-thiazolyl)-2-methoxyimino-acetamido]-ceph-3-eme-4-carboxylic acid were dissolved in a solution of 2.2 g of sodium diethylacetate in 4 ml of water and 20 ml of 98% ethanol and 0.5 g of activated carbon were added thereto. The mixture was stirred for 5 minutes and was filtered and the filtrate was stirred at room temperature. After about one hour, crystallization spontaneously occured and the mixture stood overnight at room temperature. The mixture was filtered and the recovered crystals were washed with a 7-1 ethanol-water mixture, with ethanol and then with ether and dried under reduced pressure for 2 hours to obtain the crystalline D form of the syn isomer of sodium 3-acetoxymethyl-7-[2-(2-(2-amino-4-thiazolyl)-2-methoxyimino-acetamido]-ceph-3-eme-4-carboxylate. The D form was confirmed by the infrared spectrum in nujol.

EXAMPLE 5

4.55 g of the syn isomer of 3-acetoxymethyl-7-[2-(2-amino-4-thiazolyl)-2-methoxyimino-acetamido]-ceph-3-eme-4-carboxylic acid were added to a solution of 0.85 g of sodium bicarbonate in 5 ml of water to obtain a viscous solution and 10 ml of 98% ethanol was added dropwise thereto. The mixture was filtered and 20 ml of ethanol were added dropwise to the filtrate with stirring at room temperature. The mixture stood to effect crystallization and was then filtered. The colorless crystals were washed with a 7-1 ethanol-water mixture and dried to obtain the D form of a sodium salt of a product identical to Example 1 as established by X-ray diffraction spectrum and infrared spectrum in nujol.

EXAMPLE 6

15 g of the syn isomer of 3-acetoxymethyl-7-[2-(2-amino-4-thiazolyl)-2-methoxyimino-acetamido]-ceph-3-eme-4-carboxylic acid were dissolved at −15° C. in a solution of 5 g of sodium acetate in 100 ml of methanol and 3 g of activated carbon were added thereto. The solution was filtered and the filtrate was heated to 20° C. to obtain crystals of a methanol solvate of the syn isomer of sodium 3-acetoxymethyl-7-[2-(2-amino-4-thiazolyl)-2-methoxyimino-acetamido]-ceph-3-eme-4-carboxylate identical to the product of Step A of Example 1.

One part of the crystals were dried under reduced pressure to eliminate methanol and the crystals free of methanol were held overnight in an atmosphere saturated with water. The resulting colorless crystals were dried under reduced pressure at room temperature to obtain crystals containing 5.2% of water (Fischer method). The X-ray diffraction spectrum and the infrared spectrum in nujol confirmed that the product was identical to the product of Example 1 and was in the D form.

The remainder of the crystals were maintained without any other treatment overnight in an atmosphere saturated with water vapor and the crystals were then dried under reduced pressure at room temperature for 2 hours. The resulting crystals contained 4.9% of water (Fischer method) and was determined to be identical to the product of Example 1 by its X-ray diffraction spectrum and infrared spectrum in nujol. The product was in the D form.

EXAMPLE 7

5.01 g of the ethanol solvate of the syn isomer of 3-acetoxymethyl-7-[2-(2-amino-4-thiazolyl)-2-methoxyimino-acetamido]-ceph-3-eme-4-carboxylic acid were dissolved at room temperature in a solution of 1.2 g of sodium acetate in 10 ml of water and 15 ml of isopropanol and the resulting solution was treated with 0.5 g of activated carbon and was filtered. 25 ml of isopropanol were added dropwise to the filtrate and after 5½ hours, the mixture was filtered. The recovered crystals were washed with an isopropanol-water mixture and dried for 3 hours at room temperature under reduced pressure. The crystals were determined to be identical to the product of Example 1 in the D form by its infrared spectrum.

EXAMPLE 8

The procedure of Example 7 was identically repeated except that acetone was used in place of isopropanol and the infrared spectrum in nujol showed the product to be in the D form and identical to the product of Example 1.

EXAMPLE 9

108.7 g of the syn isomer of 3-acetoxymethyl-7-[2-(2-amino-4-thiazolyl)-2-methoxyimino-acetamido]-ceph-3-eme-4-carboxylic acid containing 8% ethanol and 0.5% water were added at 0° to 2° C. under a nitrogen atmosphere to a stirred solution of 21.6 g of anhydrous sodium acetate, 25 ml of dimineralized water and 175 ml of anhydrous pure methanol and the resulting solution was stirred at 0° to 2° C. under nitrogen and was then passed through a heat insulated sterile filter. The filtrate was recovered at 0° to 2° C. under nitrogen in a sterile container and the filter was rinsed twice with 25 ml of anhydrous pure methanol. The sterile solution held at 0° to 2° C. under nitrogen under went normal precipitation over one hour with stirring under nitrogen in 500 ml of ethanol containing 2% of water at 18°–20° C. The resulting suspension was held with stirring under nitrogen for several hours and was then vacuum filtered. The recovered product was empasted successively with 100 ml and then 200 ml of ethanol containing 5% water and was then washed with 50 ml of ethanol containing 5% of water to obtain a damp product which was dried under reduced pressure at 20°–25° C. to obtain 96.5 g of the cystalline D form of the syn isomer of sodium 3-acetoxy-methyl-7-[2-(2-amino-4-thiazolyl)-2-methoxyimino-acetamido]-ceph-3-eme-4-carboxylate containing 4% of water and ≃0.4% of ethanol. The infrared spectrum showed it was the D form.

EXAMPLE 10

10 g of the syn isomer of 3-acetoxymethyl-7-[2-(2-amino-4-thiazolyl)-2-methoxyimino-acetamido]-ceph-3-eme-4-carboxylic acid containing 7.2% of ethanol were added to a solution of 2 g of sodium acetate in 7.5 ml of water and 20 ml of absolute ethanol and the mixture was stirred for 15 minutes, was treated with 1.5 g of activated carbon and was filtered. The filter was washed twice with 5 ml of a 9-1 ethanol-water mixture and the filtrate was added dropwise over 50 minutes with stirring at room temperature to 80 ml of ethanol which caused precipitation of the sodium salt. The mixture was stirred for 2 hours at 0° C. and was vacuum filtered. The crystals were washed with ethanol and dried under reduced pressure to obtain 8.45 g of the crystalline D form of the syn isomer of sodium 3-acetoxymethyl-7-[2-(2-amino-4-thiazolyl)-2-methoxyimino-acetamido]-ceph-3-eme-4-carboxylate containing 5.7% of water.

EXAMPLE 11

The process of Example 10 was repeated through the activated carbon treatment and the filtrate was added dropwise with stirring over 2 hours at room temperature to 80 ml of isopropanol. The mixture was stirred for 2 hours at room temperature and then 2 hours at 0° C. and was then vacuum filtered. The recovered crystals were washed with ethanol and were dried under reduced pressure to obtain 8.80 g of the product of Example 10 containing 0.74% water.

EXAMPLE 12

10 g of the formate solvate of the syn isomer of 3-acetoxymethyl-7-[2-(2-amino-4-thiazolyl)-2-methoxyimino-acetamido]-ceph-3-eme-4-carboxylic acid (described in Belgium Pat. No. 850,662) were added at room temperature to a solution of 3.5 g of sodium acetate in 5 ml of water and 300 ml of ethanol and when dissolution was complete, the mixture was filtered. The filtrate was added dropwise over one hour with stirring at room temperature to 160 ml of absolute ethanol and the resulting mixture was stirred at room temperature for 3 hours and at 0° C. for 16 hours. The mixture was vacuum filtered and the crystals were washed with ethanol and dried under reduced pressure to obtain 7.75 g of the crystalline D form of the syn isomer of sodium 3-acetoxymethyl-7-[2-(2-amino-4-thiazolyl)-2-methoxyimino-acetamido]-ceph-3-eme-4-carboxylate containing 0.95% of water.

EXAMPLE 13

Injectable preparations were prepared containing 500 mg of the crystalline D form of the syn isomer of sodium 3-acetoxymethyl-7-[2-(2-amino-4-thiazolyl)-2-methoxyimino-acetamido]-ceph-3-eme-4-carboxylate and sufficient sterile aqueous excipient for a final volume of 5 ml. Gelules were prepared containing 250 mg of the same sodium salt with sufficient excipient to obtain a final weight of 400 mg.

PHARMACOLOGICAL DATA

A. In Vitro Activity

The method used was a dilution of a liquid medium where a series of tubes received the same quantity of a sterile nutritive media and increasing doses of the test compounds were placed therein. Then each tube was seeded with a bacterial strain and was incubated for 24 to 48 hours at 37° C. in an oven. The increasing inhibition was determined by transillumination to determine the minimum inhibiting concentration (MIC in μg/ml) and the results are reported in the following Tables.

Product A is the crystalline D form of the syn isomer of sodium 3-acetoxymethyl-7-[2-(2-amino-4-thiazolyl)-2-methoxyimino-acetamido]-ceph-3-eme-4-carboxylate.

| STRAINS | Product A MIC in μg/ml 24 H | 48 H |
|---|---|---|
| Staphylococcus aureus I H 005 | 2 | 3 |
| Staphylococcus aureus I H 38 | 1 | 2 |
| Staphylococcus aureus I H 41 | 1 | 2 |
| Staphylococcus aureus I H 47 | 2 | 2 |
| Escherichia Coli 7881 | 0,1 | 0,1 |
| Escherichia Coli T 55 4376 | 0,1 | 0,1 |
| Escherichia Coli T 55 4076 | 0,05 | 0,05 |
| Escherichia Coli A 223 | 0,1 | 0,1 |
| Klebsiella Pneumoniae COc 229 | 0,1 | 0,1 |
| Klebsiella Pneumoniae COc 238 | 0,2 | 0,2 |
| Proteus Mirabilis 3477 | 0,05 | 0,05 |
| Proteus Mirabilis 1816 | 0,05 | 0,05 |
| Proteus Mirabilis 9048 | 0,02 | 0,02 |
| Proteus Vulgaris Co 1 | 0,2 | 0,4 |
| Proteus Vulgaris Co 4 | 0,6 | 0,6 |
| Proteus Vulgaris Du 27 | ≦0,02 | ≦0,02 |
| Salmonella typhimurium 6478 | 0,1 | 0,1 |

B. Stability Test

Product A was placed in a flask containing nonsterile air and it was closed with a rubber stopper. The flask was stored at the temperatures for the times indicated in the following table and the percent of activity remaining was determined.

| Temperature | % of activity after | | | | |
|---|---|---|---|---|---|
| | 0 | 160 hours | 2 weeks | 1.5 months | 3 months |
| 80° C. | 97 | 89.5 | 81.5 | — | — |
| 50° C. | 97 | — | — | 92.5 | 92 |

Various modifications of the products and processes of the invention may be made without departing from the spirit or scope thereof and it should be understood that the invention is intended to be limited only as defined in the appended claims.

We claim:

1. The stable crystalline hydrate of D form of the syn isomer of sodium 3-acetoxymethyl-7-[2-(2-amino-4-thiazolyl)-2-methoxyimino-acetamido]-ceph-3-eme-4-carboxylate having the formula

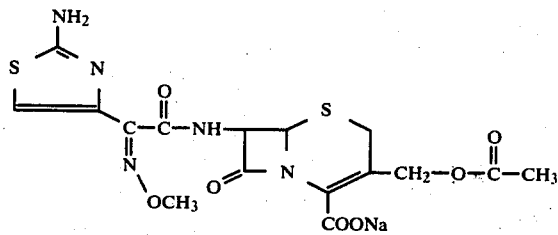

having the infrared spectrum in nujol of FIG. 1 and having the following X-ray powder diffraction diagram obtained with the Kα copper radiation at a wave length λ=1.54 A° wherein inter-recticular intervals are indicated as d and the relative intensities are indicated as $I/I_1$:

| d | $I/I_1$ |
|---|---|
| 9.3 | 0.95 |
| 8.8 | 0.09 |
| 6.5 | 0.07 |
| 6.46 | 0.06 |
| 6.10 | 0.13 |
| 5.30 | 0.25 |
| 5.12 | 0.05 |
| 5.03 | 0.04 |
| 4.57 | 0.04 |
| 4.40 | 0.17 |
| 4.20 | 0.29 |
| 3.96 | 0.70 |
| 3.88 | 0.18 |
| 3.76 | 0.34 |
| 3.6 | 1.00 |
| 3.41 | 0.15 |
| 3.27 | 0.09 |

-continued

| d | $I/I_1$ |
|---|---|
| 3.19 | 0.11 |
| 3.13 | 0.13 |
| 3.10 | 0.13 |
| 3.03 | 0.15 |
| 2.97 | 0.06 |
| 2.78 | 0.07 |
| 2.72 | 0.04 |
| 2.69 | 0.04 |
| 2.60 | 0.19 |
| 2.50 | 0.11 |
| 2.44 | 0.05 |
| 2.40 | 0.08 |
| 2.32 | 0.09 |
| 2.25 | 0.05 |

2. An antibiotic composition comprising an antibiotically effective amount of the compound of claim 1 and a pharmaceutical carrier.

3. A method of combatting bacterial infection, in warm-blooded animals comprising internally administering to warm-blooded animals an antibiotically effective amount of the compound of claim 1.

4. A process for the preparation of the compound of claim 1 comprising reacting a compound selected from the group consisting of the syn isomer of 3-acetoxymethyl-7-[2-(2-amino-4-thiazolyl)-2-methoxyiminoacetamino]-ceph-3-eme-4-carboxylic acid, its hydrate, its ethanol solvate, its formic acid solvate, mixtures of hydrate and ethanol and formic acid solvate with the sodium salt of an organic acid selected from the group consisting of sodium acetate, sodium diethylacetate and sodium 2-ethylhexanoate in aqueous methanol at about 0° C., mixing the methanolic solution of the sodium salt with ethanol containing 0.5 to 10% by weight of water, allowing the resulting suspension to stand and recovering the crystalline hydrate of the compound of claim 1.

* * * * *